United States Patent
Barta et al.

(12) 
(10) Patent No.: US 6,245,921 B1
(45) Date of Patent: Jun. 12, 2001

(54) PROCESS FOR THE ISOLATION OF PSEUDOMONIC ACID A FROM PSEUDOMONIC ACID COMPLEX-CONTAINING CULTURE BROTH

(75) Inventors: Istvan Barta; Aniko Tegdes; Valeria Szell, all of Budapest; Csaba Szabo, Debrecen; Edit Nagy Nee Arvai, Debrecen; Vilmos Keri, Debrecen, all of (HU); David Leonov, Rehovat (IL); Ildiko Lang; Margit Bidlo Nee Igloy, both of Budapest (HU); Gyula Jerkovich, Budakeszi; Janos Salat, Budapest, both of (HU)

(73) Assignee: Biogal Gyogyszergyar Rt., Debrecen (HU)

( * ) Notice: Subject to any disclaimer, the term of this patent is extended or adjusted under 35 U.S.C. 154(b) by 0 days.

(21) Appl. No.: 09/497,806

(22) Filed: Feb. 3, 2000

Related U.S. Application Data

(60) Provisional application No. 60/118,447, filed on Feb. 3, 1999.

(51) Int. Cl.[7] ................................................. C07D 315/00
(52) U.S. Cl. .............................................................. 549/417
(58) Field of Search ............................................... 549/417

(56) References Cited

U.S. PATENT DOCUMENTS 4,289,703 9/1981 Barrow et al. .

FOREIGN PATENT DOCUMENTS

| 870855 | 3/1979 | (BE) . |
| 2227739 | 6/1973 | (DE) . |
| 0 005 614 | 11/1979 | (EP) . |
| 52-70083 | 6/1977 | (JP) . |

OTHER PUBLICATIONS

J.P. Clayton et al., "The Structure and Configuration of Pseudomonic Acid C", Tetrahedron Letters, vol. 21, pp 881–884. 1980.

Sir Ernst B. Chain, G. Mellows, "Pseudomonic Acid. Part 3[1]. Structure of Pseudomonic Acid B", Journal of The Chemical Society, Perkin Transactions I, 1977, pp 318–322.

Peter J. O'Hanlon, Nornan H. Rogers, "The Chemistry of Pseudomonic Acid. Part 6.[1] Structure and Preparation of Pseudomonic Acid D", Journal of The Chemical Society, Perkins Transactions I, 1983, pp. 2655–2657.

Julia Hughes and Graham Mellows, "Interaction of pseudomonic acid A with *Escherichia coli* B isoleucyl–tRNA snythetase", The Biochemical Journal, vol. 191, 1980, pp 209–219.

*Primary Examiner*—Joseph K. McKane
*Assistant Examiner*—Taofiq A. Solola
(74) *Attorney, Agent, or Firm*—Kenyon & Kenyon

(57) ABSTRACT

A process for the isolation of the pseudomonic acid A antibiotic of pharmaceutical quality from the culture broth of one of the pseudomonic acid A-producing species of the Pseudomonas bacterium genus comprising the extraction of the biosynthesized pseudomonic acid A from the culture broth at acidic pH with a chlorinated aliphatic hydrocarbon or isobutyl acetate, followed by purification, is disclosed. The invention includes processes for purification of the isolated pseudomonic acid A, including (a) by the distribution of the evaporated extract residue between the aqueous-alcohol and some aliphatic or aromatic hydrocarbon, and then the extraction of the increased water-containing aqueous-alcoholic phase with methylene chloride, ethyl acetate, or isobutyl acetate; (b) by the extraction of the extract with aqueous ammonium hydrogen carbonate, alkali metal hydroxide or ammonium hydroxide solution and the acidification of the resulting alkaline aqueous extract, then reextraction again with a chlorinated aliphatic hydrocarbon or isobutyl acetate; and (c) by the concentration of the extract and the recrystallization of the crystalline pseudomonic acid A in a mixture of isobutyl acetate and petroleum ether, or acetonitrile, or aqueous acetonitrile.

17 Claims, No Drawings

PROCESS FOR THE ISOLATION OF PSEUDOMONIC ACID A FROM PSEUDOMONIC ACID COMPLEX-CONTAINING CULTURE BROTH

This appln claims the benefit of No. 60/118,447 filed Feb. 3, 1999.

FIELD OF THE INVENTION

The present invention relates to a process for the isolation of pseudomonic acid A (mupirocin) from a pseudomonic acid complex-containing culture broth.

BACKGROUND OF THE INVENTION

Pseudomonic acid A, also known as mupirocin, is an antibiotic having the formula (I):

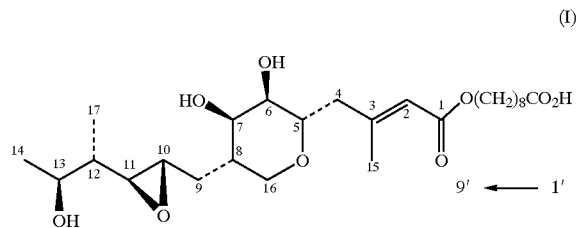

(I)

It is known that *Pseudomonas fluorescens* strains are able to biosynthesize, in addition to pseudomonic acid A, other related antibiotics designated by the letters B–D in small quantities [E. B. Chain, G. Mellows, J. Chem. Soc. Perkin Trans I. 318 (1977); J. P. Clayton et al., Tetrahedron Lett., 21, 881 (1980); P. J. O. Hanlon, N. H. Rogers, J. Chem. Soc. Perkin Trans I. 2665 (1983)], represented by formulas (II)–(IV), respectively:

Among the pseudomonic acid antibiotics, from a therapeutic point of view the most valuable is pseudomonic acid A, which has a growth inhibiting effect mainly against Gram positive bacteria (e.g. *Staphylococcus aureus, Streptococcus pyogenes, Streptococcus pneumoniae, Klebsiella pneumoniae*) and some Gram negative bacteria (e.g., *Haemophilus influenzae, Neisseria gonorrhoeae*) and its minimal inhibiting concentration is in the range of 0.02–0.5 $mg/dm^3$. Pseudomonic acid A, by inhibiting the isoleucine-tRNA synthase enzyme, has an effect on the peptide synthesis of pathogen bacteria [J. Hughes and G. Mellows, Biochem. J. 191, 209–219, (1980)]. An advantageous feature of this antibiotic is that it is less toxic for both humans and animals and it is negative in the Ames test. Pseudomonic acid A is presently used in human therapy, in various formulations, for the treatment of skin infections (e.g. impetigo, pyoderma), nose and external ear infections, acne, burns, eczema, psoriasis, in case of ulceration for treatment of secondary infections, and for prevention of hospital infections.

One method for the isolation of pseudomonic acid A from the antibiotic complex-containing culture broth is the liquid-liquid extraction. According to German Patent No. 2,227,739 and U.S. Pat. No. 4,289,703, soluble barium salts are added to the fermentation broth, then the microorganism cells with the insoluble inactive agents are separated by centrifugation and finally the antibiotics are extracted by methyl isobutyl ketone. The antibiotics are then removed from the methyl isobutyl ketone extract by alkaline water and the resulting alkaline aqueous extract is cleaned by reextraction with methyl isobutyl ketone. The crude product obtained is chromatographed, and an ester derivative is prepared from the pseudomonic acid antibiotic complex and purified with preparative thin layer chromatography. The acid form of the pure antibiotic is obtained by hydrolysis.

Belgian Patent No. 870,855 relates to a process in which the culture broth is extracted with methyl isobutyl ketone and from the extract the active substance is extracted by sodium hydrogen carbonate solution. Materials insoluble in

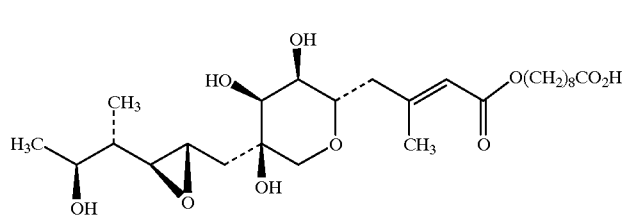

(II)

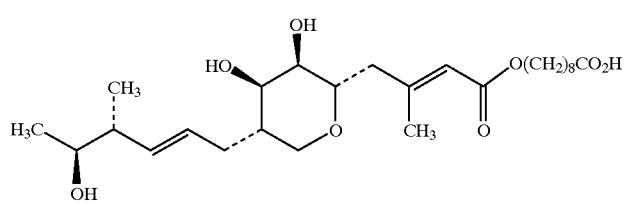

(III)

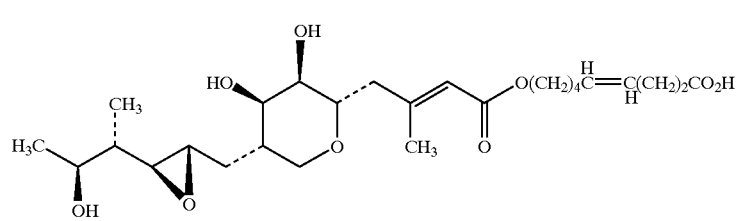

(IV)

alkaline water are separated by filtration, then the pH of the filtrate is acidified and extracted by methyl isobutyl ketone. Finally the pseudomonic acid A is obtained by the concentration of the extract and crystallization from a methyl isobutyl ketone-n-heptane mixture.

Japanese Patent No. 52-70083 relates to two methods for the recovery of pseudomonic acid A from a culture broth. According to one of these methods, the bacterium cells are separated from the culture broth by centrifugation, then the active substance is extracted from the supernatant by ethyl acetate. Then the pseudomonic acid complex is reextracted from the ethyl acetate phase by sodium hydrogen carbonate solution and after acidification it is extracted again with ethyl acetate. After evaporation the residue is purified on silicagel column by the application of chloroform-methanol eluents and finally the pure pseudomonic acid A is reached by crystallization from diisopropyl ether. In the other process the crude product obtained by the above method is chromatographed on DEAE-Sephadex anion exchange column by the application of methanol-ammonia eluent and the pseudomonic acid A containing fractions are separated.

A. D. Curzons described the recovery of pseudomonic acid A from culture broth by lithium salt formation (European Patent No. 0 005 614). The active ingredient-containing methyl isobutyl ketone extract obtained at pH 4.5 is reacted with lithium 2-ethyl-hexanoate dissolved in methanol. Precipitated pseudomonic acid A lithium salt is separated, dissolved in water and the pseudomonic acid A released at pH 4.5 is extracted in methyl isobutyl ketone and precipitated in the presence of n-heptane.

In the methods discussed above, polar and water-immiscible solvents (methyl isobutyl ketone, ethyl acetate, n-butanol) are used for the recovery of the pseudomonic acid complex from the culture broth. According to our experience, selective extraction can not be realized satisfactorily using these processes, since besides the pseudomonic acid complex other polar and nonpolar impurities are also extracted in large quantities. Pseudomonic acid A can be recovered in pure form only with low yield (17–34%) by alkaline extraction of the organic solvents containing the impurities in large quantities, then by organic solvent reextraction at acidic pH, and then by crystallization of the crude product. The use of chromatographic processes for purification is not advantageous on a production scale because of their high labor cost and solvent demand. In addition, in the presence of chromatographic adsorbents and during the chromatographic process intramolecular transformations take place in the active substance, which lead to the formation of the biologically inactive bicyclic compound 9-{4-[1S,6R-8R(1S,3S-dihydroxy-2S-methyl-butyl)-5S-hydroxy-3,7-dioxabicyclo[4.3.0]nonane-4S-yl]-3-methyl-but-2(E)-enoyloxy}nonanoic acid (formula V)

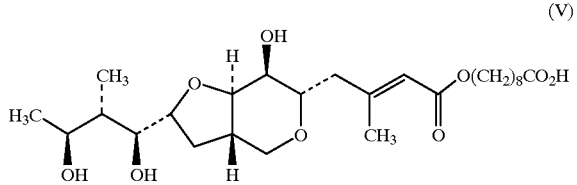

(V)

and the compound 9-{4-[1R,6S-4S,10S-dihydroxy-3R-(2S-hydroxy-1S-methyl-propyl)-2,8-dioxabicyclo[4.4.0]decane-9S-yl]-3-methylbut-2(E)-enoyloxy}nonanoic acid (formula VI).

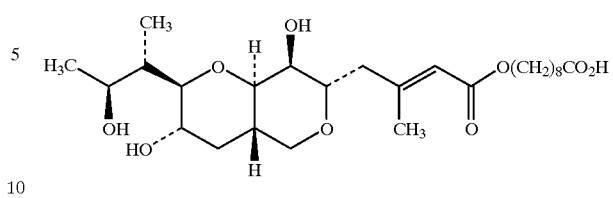

(VI)

Formation of these compounds and their elimination via recrystallization considerably reduces the recovery yield of the pseudomonic acid A.

Although the isolation process through the intermediate of pseudomonic acid A lithium salt does not contain any chromatographic step, it is not convenient for a production scale process, since the lithium salt used in the process makes the process complicated and expensive to use on a production scale.

Thus there remains a need in the art for a new process for the isolation of the antibiotic pseudomonic acid A, which is free from the disadvantages of the known processes and the application of which in production scale results in a high yield of the recovery of the above-mentioned antibiotic.

SUMMARY OF THE INVENTION

The present invention is directed to a process for the isolation of the pseudomonic acid A antibiotic of formula (I)

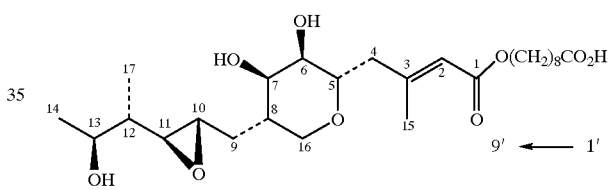

(I)

comprising the steps of extracting pseudomonic acid A from a culture of a pseudomonic acid A-producing species of the Pseudomonas bacterium genus, at acidic pH, using a chlorinated aliphatic hydrocarbon or isobutyl acetate, such that a pseudomonic acid A-containing extract is obtained; and purifying the pseudomonic acid A from said extract. Optionally the purified pseudomonic acid A is crystallized.

In one embodiment of the present invention, the purifying step comprises distributing the evaporation residue of the extract between aqueous-alcohol and less polar solvents in order to remove impurities; diluting the aqueous-alcohol phase with water; and extracting with a more polar solvent to remove the purified pseudomonic acid A.

In another embodiment of the present invention, the purifying step comprises recovering pseudomonic acid A from the extract with an aqueous solution of ammonium hydrogen carbonate, an alkali metal hydroxide or ammonium hydroxide, such that an alkaline solution is formed; acidifying the alkaline solution such that an acidic solution is formed; and extracting the acidic solution with a chlorinated aliphatic hydrocarbon or isobutyl acetate.

DETAILED DESCRIPTION OF THE INVENTION

It has surprisingly been found that pseudomonic acid A efficiently and selectively can be extracted after acidification both from the microbial cell-containing whole broth, and from the supernatant obtained after the separation of the cells, by chlorinated aliphatic hydrocarbons, then the majority of the inactive impurities accompanying the pseudomonic acid A can be eliminated from the crude product after the evaporation of the above extract by the distribution of the evaporation residue between an aqueous-alcohol solution and an aliphatic hydrocarbon, then between aqueous alcohol and an aromatic hydrocarbon. Preferably the alcohol is methanol. Using this method, from the crude product pseudomonic acid A can be obtained in medicament quality after recrystallization from isobutyl acetate, acetonitrile or a water-acetonitrile mixture.

According to a preferred method of the present invention, during the isolation of the pseudomonic acid A antibiotic the microorganism cells are separated at nearly neutral pH by centrifugation. After the centrifugation of the culture broth at nearly neutral pH the major part of the pseudomonic acid A is in the supernatant and it can be recovered by extraction from the supernatant, preferably at pH 4.5. Preferably, the extraction of the antibiotic is done by a chlorinated aliphatic hydrocarbon, most preferably by methylene chloride.

Primary purification of the pseudomonic acid A in the methylene chloride extract can be carried out by the application of distribution separation. Possible pigments and lipid impurities of the crude product can be separated by the distribution between 10% water-containing water-methanol mixture and an aliphatic hydrocarbon such as n-hexane or n-heptane. The major part of the lipid type nonpolar inactive impurities are transferred into the n-hexane or n-heptane phase. By increasing the water content of the water-methanol phase up to 25% and extracting it using an aromatic hydrocarbon, preferably using toluene, the more polar inactive impurities can be eliminated from the crude product.

By increasing the water content of the water-methanol phase to 50% and extracting it by a water-immiscible solvent, preferably by methylene chloride, ethyl acetate, methyl isobutyl ketone, n-butyl-acetate, or isobutyl acetate, and evaporating the organic solvent, the pseudomonic acid A-containing crude product is obtained. Pseudomonic acid A can be separated from other components of the pseudomonic acid complex being formed during the biosynthesis by crystallization, preferably using a methyl isobutyl ketone-n-heptane solvent mixture.

In another embodiment of the present invention, the whole broth extraction may be done in the presence of the microorganism cells at pH 4.5 by a chlorinated aliphatic hydrocarbon, preferably by methylene chloride. The pseudomonic acid complex is extracted from the methylene chloride extract by 2% sodium hydrogen carbonate solution and the pseudomonic acid complex is obtained in acidic form from the water phase, preferably at pH 4.5, by methylene chloride.

Furthermore, it has also been recognized that after acidifying, the pseudomonic acid A dissolved in the broth and bound to the cells of the biomass can be extracted efficiently and selectively by using isobutyl acetate for the extraction. It has also been found that after the culture broth extraction the pseudomonic acid A can be recovered from the isobutyl acetate extract more favorably by ammonium hydrogen carbonate, ammonium hydroxide or an alkali metal hydroxide. A preferred alkali metal hydroxide is sodium hydroxide. After acidification of the above extracts, and extracting them by isobutyl acetate, a concentrated organic solvent extract can be obtained from which a crystalline crude product can be prepared by evaporation. After recrystallization of the latter from isobutyl acetate, acetonitrile and/or a water-acetonitrile mixture the pseudomonic acid A can be obtained in medicament quality.

According to a preferred embodiment of the present invention, the extraction of the antibiotic from the whole broth is done by isobutyl acetate, preferably at a pH of about 4.5. In order to eliminate the formation of an emulsion, a demulsifier, preferably Armogard D5397 (AKZO Chemicals Ltd., Lancashire, Great Britain) may be used. Preferably the demulsifier comprises about 0.1% in 10 vol. % isobutyl acetate solution. From the isobutyl acetate extract separated on a Westfalia type separator the pseudomonic acid complex is recovered with aqueous sodium hydroxide solution, and the crude product obtained after the extraction at acidic pH is crystallized from a petroleum ether (boiling range: 60–95° C.) and isobutyl acetate solvent mixture. The product obtained is recrystallized, preferably from acetonitrile; subsequently the aqueous solution is kept at rest, then recovered after filtration.

Any culture broth of any microorganism strain of Pseudomonas bacterium genus able to biosynthesize pseudomonic acid A is suitable for use as a starting material for the method of the present invention.

For the acidic treatment of the microorganism cells, both mineral acids such as hydrochloric acid, sulfuric acid and phosphoric acid and organic acids such as acetic acid and oxalic acid can be used. Oxalic acid and sulfuric acid are particularly advantageous for this purpose.

At the end of the fermentation, the exact content of the pseudomonic acid A and related compounds are determined by high pressure liquid chromatography. The culture broth is diluted to twice by ethanol, ultrasonic treated, and centrifuged, and the supernatant is used for the analysis. Pseudomonic acid A and related compounds prepared using the method of the present invention were found to have the following retention times: pseudomonic acid A of formula (I) 8.34 min, pseudomonic acid B of formula (II) 6.83 min, pseudomonic acid C of formula (111) 16.8 min, pseudomonic acid D of formula (IV) 6.8 min, minor component of formula (V) 6.55 min, minor component of formula (VI) 6.9 min [machine: LKB 2248 pump, LKB 2157 autosampler, LKB 2155 column oven, LKB 2141 UV detector, analysis at 222 nm, column: Nucleosil $C_{18}$ 10 $\mu$m (BST), eluent: mixture (35:65) of acetonitrile and aqueous 0.1 M $NaH_2PO_4$ solution (pH=4.2), flow rate 1.0 ml/min].

The structure of the isolated pseudomonic acid A was determined by UV, IR, $^1$H-NMR, $^{13}$C-NMR and mass spectroscopic examinations. Pseudomonic acid A prepared in accordance with the present invention was identical to polymorphic form I published in the international patent no. WO92/10493.

The process according to the present invention is illustrated by the following examples. However, the present invention should not be construed as limited thereby.

EXAMPLES

Example 1

The pH of a 5 liter culture broth with 1200 $\mu$g/ml mupirocin was adjusted under continuous stirring to 4.5 by 20% sulfuric acid (60 ml). The acidified liquor was extracted by 2.5 liters methylene chloride. The phases were then separated and a sharp phase was prepared from the emulsified organic phase by centrifugation. According to the previous step the culture broth was extracted twice again with 1.25 liter methylene chloride. The combined methylene chloride extracts were washed with 1.25 liter deionized water. The phases were separated and, at below 20° C., the methylene chloride extract was extracted first with 0.5 liter and then with 0.25 liter 2% sodium hydrogen carbonate solution. The phases were separated and the extracts were combined. The combined extract was cooled to below 20° C. and the pH of the extract was adjusted under continuous stirring to 4.5 by 20% sulfuric acid. The acidic solution obtained was extracted one time with 0.38 liter and one time with 0.19 liter methylene chloride. The combined methylene chloride extracts were washed with 0.19 liter deionized water, then the methylene chloride extract was clarified at room temperature with charcoal (0.42 g). After clarifying the methylene chloride extract was evaporated. The evaporation residue (about 8 g) was dissolved at room temperature in 16 ml isobutyl acetate. Under stirring the solution was cooled to 0–5° C. and the stirring was continued until the onset of the crystallization. Then the crystallization was carried out at this temperature overnight.

Precipitated mupirocin was filtered, then cover washing was done by 2×4 ml cold (below 5° C.) isobutyl acetate and by 6 ml mixture (1:2) of isobutyl acetate-petroleum ether. After this the antibiotic was washed by suspension in 2×25 ml petroleum ether (boiling range: 60–95° C.) and dried in vacuum at 50° C. The mupirocin obtained was dissolved at 40–45° C. in 60 ml isobutyl acetate. The solution was cooled to room temperature, and 60 ml petroleum ether (boiling range: 60–95° C.) was introduced drop by drop into the solution. Then the crystallization was carried out at 0–5° C. overnight. Precipitated crystals were filtered and the cover washing was done by 2×4 ml cold (below 5° C.) isobutyl acetate-petroleum ether mixture (1:2). Then the product was washed by suspending it in 3×20 ml petroleum ether. The mupirocin was dried in vacuum at 50° C. temperature until constant weight. In this way 3.3 g pure mupirocin was obtained having the following characteristics:

Melting point: 73–75° C.

Ultraviolet spectrum (10 μg/ml, in 95% ethanol solution): $\lambda_{max}$=222 nm $E^{1\%}_{1\ cm}$=303.6.

Infrared spectrum (KBr): νOH 3483 and 3306, νC=O 1728 (COOCH$_2$), 1720 (COOH) cm$^{-1}$ $^1$H-NMR spectrum (CDCl$_3$, $\delta_{TMS}$=0.00 ppm):

| δ (ppm) | Assignment | Coupling constant (Hz) |
|---|---|---|
| 5.75 (1H)q | 2-H | $^4J_{2,15}$ = 1.1 |
| 4.08 (2H)t | 9'-H$_2$ | $^3J_{8,9}$ = 6.4 |
| 3.93–3.72 (4H)m | 5,7,13-H; 16-H$_\alpha$ | |
| 3.55 (1H)dd | 16-H$_\beta$ | $^2J_{16\alpha,16\beta}$ = 11.8; $^3J_{16\alpha,8}$ = 2.6 |
| 3.48 (1H)dd | 6-H | $^3J_{5,8}$ = 8.4 $^3J_{6,7}$ = 3.2 |
| 2.82 (1H)td | 10-H | $^3J_{9,10}$ = 6.3; $^3J_{10,11}$ = 2.3 |
| 2.74 (1H)dd | 11-H | $^3J_{10,11}$ = 2.3; $^3J_{11,12}$ = 7.8 |
| 2.60 (1H)dd | 4-H$_\alpha$ | $^3J_{4\alpha,4\beta}$ = 14.5; $^3J_{4\alpha,5}$ = 2.7 |
| 2.36–2.28 (3H)m | 4-H$_\beta$; 2'-H$_2$ | |
| 2.20 (3H)d | 15-H$_3$ | $^4J_{2,15}$ = 1.1 |
| 2.02–1.92 (1H)m | 8-H | |
| 1.76–1.61 (6H)m | 9-H$_2$; 3'-H$_2$; 8',-H$_2$ | |
| 1.43–1.33 (9H)m | 12-H; 4'-H$_2$; 5'-H$_2$; 6'-H$_2$; 7'-H$_2$ | |
| 1.22 (3H)d | 14-H$_3$ | $^3J_{13,14}$ = 6.4 |
| 0.94 (3H)d | 17-H$_3$ | $^3J_{12,17}$ = 7.0 |

$^{13}$C-NMR spectrum (CDCl$_3$ solution, $\delta_{TMS}$=0.00 ppm):

| δ (ppm) | Assignment | δ (ppm) | Assignment |
|---|---|---|---|
| 177.8s | C-1' | 42.7t, d | C-9, C-12 |
| 166.9s | C-1 | 39.4d | C-8 |
| 156.0s | C-3 | 33.9t, t | C-9, C-2' |
| 117.7d | C-2 | 31.6t | C4'* |
| 74.9d | C-5 | 28.9t | C-5'* |
| 71.4d | C-13 | 28.8t | C-6'* |
| 70.4d | C-7 | 28.5t | C-8'* |
| 69.0d | C-6 | 25.9t | C-7' |
| 65.3t | C-16 | 24.6t | C-3' |
| 63.9t | C-9' | 20.8q | C-14 |
| 61.3d | C-11 | 19.1q | C-15 |
| 55.6d | C-10 | 12.7g | C-17 |

*replaceable assignments

Mass spectrum:
Characteristic spectral data:

| m/z | RI(%) | Assignment |
|---|---|---|
| 501 | 100 | (M + H)$^+$ |
| 327 | 45 | (M + H − HO/CH$_2$/$_8$COOH)$^+$ |
| 309 | 16 | (m/z 327-H$_2$O)$^+$ |
| 227 | 33 | (C$_{12}$H$_{19}$O$_4$)+ |

Example 2

The pH of a 5 liter culture broth possessing 1500 μg/ml mupirocin was adjusted under continuous stirring to 4.5 by 20% sulfuric acid. The acidified liquor was extracted by 2.5 liter isobutyl acetate. Phases were separated and a sharp phase was prepared from the emulsified organic phase by centrifugation. According to the previous step the culture broth was extracted again with 1.25 liter isobutyl acetate. The combined isobutyl acetate extracts were washed with 1.25 liter deionized water. The phases were separated and 0.5 liter deionized water was added to the isobutyl acetate extract. The pH of the mixed phase was adjusted to 8.0±0.2 by 5% ammonium hydroxide. The phases were separated and the isobutyl acetate extract was extracted again with 0.5 liter deionized water at pH 8.0±0.2. The combined alkaline extract was cooled below 20° C. and the pH of the extract was adjusted under continuous stirring to 4.5 by 20% sulfuric acid. The acidic solution obtained was extracted one time with 0.5 liter and then one time with 0.25 liter isobutyl acetate. The combined isobutyl acetate extracts were washed with 0.25 liter deionized water, then the isobutyl acetate extract was clarified at room temperature with 0.52 g charcoal. After clarifying the isobutyl acetate extract was concentrated in vacuum to a final volume of 13 ml. Then the crystallization and the recrystallization of mupirocin were done as in Example 1. In this way 3.75 g mupirocin was obtained, having the same physical properties as described in Example 1.

Example 3

80 liter culture broth with 1000 µg/ml mupirocin concentration was centrifuged with an F-100 type super centrifuge (manufacturer: Budapesti Vegyipari Gépgyár), then the pH of the supernatant was adjusted to 4.5 with oxalic acid (about 0.69 liter). The acidified solution was extracted twice by 24 liter methylene chloride, and the combined extracts were evaporated in vacuum. The oily residue (about 0.14 kg) was dissolved in 0.56 liter 10% water containing methanol and then the solution was extracted twice by 0.56 liter n-hexane. The methanolic solution was diluted by deionized water to 25% water content and the solution was extracted twice with 0.56 liter toluene. Subsequently the methanolic solution was diluted with deionized water to 50% water content and the solution was extracted one time with 0.56 liter methylene chloride, then one time with 0.28 liter methylene chloride. The combined methylene chloride extracts were evaporated in vacuum. The evaporation residue obtained (about 0.11 kg) was processed according to the Example 1, resulting in 44 g mupirocin, having the same physical properties as in Example 1.

Example 4

The pH of 160 liter culture broth containing mupirocin in 1200 µg/ml concentration was adjusted under continuous stirring to 4.5±0.2 by 20% sulfuric acid (about 2.7 liters). After this the acidified liquor was extracted by 80 liters isobutyl acetate. After 30 min stirring 0.1% demulsifier was added into it (1 g Armogard D5397/liter broth in a solution of isobutyl acetate). The phases were separated by a SA1-01-175 type Westfalia separator (Westfalia Separator A.G., Oelde, Germany). The culture broth was extracted again with 40 liters isobutyl acetate and separated according to the previous step. The isobutyl acetate extract was washed with 40 liters deionized water. The washed isobutyl acetate extract was mixed with 20 liters deionized water, and then 400 ml 10 mass % magnesium sulfate solution was added to the mixture as a demulsifier. Subsequently the pH of the aqueous isobutyl acetate mixture was adjusted by sodium hydroxide to 8.0±0.2. After 20 min stirring the phases were separated, and the isobutyl acetate extract was extracted again at pH 8.2±0.2. The combined aqueous alkaline solution was extracted with 12 liters isobutyl acetate in the presence of 800 ml 10 mass % magnesium sulfate. After separation of the phases, 8 liters isobutyl acetate was added to the aqueous phase, then the pH of the aqueous isobutyl acetate mixture was adjusted to 4.5±0.2 by 20% sulfuric acid solution. After 20 min stirring the phases were separated, and the acidic solution was extracted again as it was written before. The combined isobutyl acetate extracts were washed with 5 liters deionized water in the presence of 100 ml 10 mass % magnesium sulfate solution. The phases were separated, and the isobutyl acetate extract was evaporated in vacuum to 1.1 liter final volume. The isobutyl acetate concentrate was mixed with 110 ml petroleum ether (boiling range: 60–95° C.), and the crystallization was carried out at 0–5° C. for 24 hours. Precipitated crystals were filtered and washed with cold (below 5° C.) isobutyl acetate. Then the wet crude product was suspended in 600 ml petroleum ether, filtered and dried in vacuum at 40° C. The mupirocin obtained was dissolved in 550 ml acetonitrile at 40–50° C., and clarified at the previous temperature with charcoal (5.5 g). After clarifying the solution was cooled to room temperature, then kept at 0–5° C. for 24 hours. The precipitated mupirocin was filtered, then the cover washing was done by 50 ml cold (below 5° C.) acetonitrile. Wet crystals were suspended in 200 ml deionized water, then another 200 ml quantity of deionized water was added to the suspension. Then the crystallization was done at 0–5° C. for 24 hours. The crystals were filtered and cover washing was done with 2×50 ml deionized water. The product was dried under vacuum at 40° C. for 72 hours. In this way 80.6 g mupirocin was obtained, having the same physical properties as in Example 1.

Although certain presently preferred embodiments of the invention have been described herein, it will be apparent to those skilled in the art to which the invention pertains that variations and modifications of the described embodiment may be made without departing form the spirit and scope of the invention. Accordingly, it is intended that the invention be limited only to the extent required by the appended claims and the applicable rules of law.

We claim:

1. A process for the isolation of the pseudomonic acid A antibiotic of formula (I)

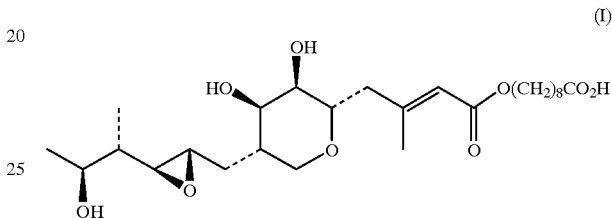

comprising the steps of:

extracting pseudomonic acid A from a culture of a pseudomonic acid A-producing species of the Pseudomonas bacterium genus, at acidic pH, using a chlorinated aliphatic hydrocarbon or isobutyl acetate, such that a pseudomonic acid A-containing extract is obtained; and purifying the pseudomonic acid A from said extract by distributing the extract between an aqueous phase and an organic phase comprising at least one organic solvent and evaporating the organic solvent.

2. The process of claim 1 wherein the the aqueous phase is a solution comprising water and an alcohol.

3. The process of claim 2, wherein said alcohol is methanol.

4. The process of claim 3, wherein the extract is distributed between a 10% water-methanol solution and an aliphatic hydrocarbon.

5. The process of claim 4, wherein the aliphatic hydrocarbon is hexane or heptane.

6. The process of claim 5, wherein the aliphatic hydrocarbon is n-hexane.

7. The process of claim 3, wherein the extract is distributed between a 25% water-methanol solution and an aromatic hydrocarbon.

8. The process of claim 7, wherein the aromatic hydrocarbon is toluene.

9. The process of claim 3, wherein the extract is distributed between a 50% water-methanol solution and a water-immiscible solvent.

10. The process of claim 9, wherein said water-immiscible solvent is selected from the group consisting of methylene chloride, ethyl acetate, methyl isobutyl ketone, n-butyl acetate and isobutyl acetate.

11. A process for the isolation of the pseudomonic acid A antibiotic of formula (I)

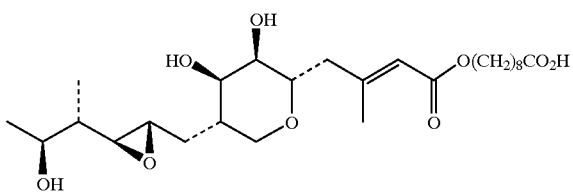

(I)

comprising the steps of:
  extracting pseudomonic acid A from a culture of a pseudomonic acid A-producing species of the Pseudomonas bacterium genus, at acidic pH, using a chlorinated aliphatic hydrocarbon or isobutyl acetate, such that a pseudomonic acid A-containing extract is obtained; and
  purifying the pseudomonic acid A from said extract by recovering pseudomonic acid A from the extract with an aqueous solution of ammonium hydrogen carbonate, an alkali metal hydroxide or ammonium hydroxide, such that an alkaline solution is formed; acidifying the alkaline solution such that an acidic solution is formed; and extracting the acidic solution with isobutyl acetate.

12. The process of claim 11, wherein pseudomonic acid A is recovered from the extract with an aqueous sodium hydroxide solution.

13. The process of claim 11, wherein pseudomonic acid A is recovered from the extract with an aqueous ammonium hydroxide solution.

14. The process of claim 11, wherein pseudomonic acid A is recovered from the extract with an aqueous ammonium hydrogen carbonate solution.

15. The process of claim 1, further comprising the steps of evaporating and crystallizing the purified pseudomonic acid A.

16. The process of claim 15, wherein the crude pseudomonic acid A is crystallized from isobutyl acetate or an isobutyl acetate-petroleum ether mixture.

17. The process of claim 15, wherein the crude pseudomonic acid A is crystallized from acetonitrile, water, or a mixture of acetonitrile and water.

* * * * *